United States Patent [19]

McAlister

[11] Patent Number: 4,689,127
[45] Date of Patent: Aug. 25, 1987

[54] CONTROL OF ANODIC PASSIVATION SYSTEMS
[75] Inventor: Donald R. McAlister, Ballwin, Mo.
[73] Assignee: Monsanto Company, St. Louis, Mo.
[21] Appl. No.: 830,383
[22] Filed: Feb. 14, 1986
[51] Int. Cl.⁴ ............................................. C23F 13/00
[52] U.S. Cl. .................................... 204/147; 204/196; 165/134.1
[58] Field of Search ....................... 204/147, 196, 231; 165/134.1

[56] References Cited
U.S. PATENT DOCUMENTS

| | | | |
|---|---|---|---|
| 1,020,480 | 3/1912 | Cumberland | 204/196 |
| 3,483,101 | 12/1969 | Delahunt et al. | 204/196 |
| 3,714,004 | 1/1973 | Riggs et al. | 204/196 |
| 3,798,142 | 3/1974 | Evans | 204/147 |
| 3,841,988 | 10/1974 | Gleason | 204/196 |
| 4,138,323 | 2/1979 | Statsenko et al. | 204/196 |
| 4,345,981 | 8/1982 | Bennett et al. | 204/147 |
| 4,437,957 | 3/1984 | Freeman | 204/196 |
| 4,586,562 | 5/1986 | Carlson et al. | 204/147 |

Primary Examiner—T. Tung
Attorney, Agent, or Firm—Lawrence L. Limpus; Charles E. Krukiel

[57] ABSTRACT

A method and apparatus for controlling anodic protection of a heat exchanger using two reference electrodes disposed at opposite ends of the heat exchanger.

3 Claims, 3 Drawing Figures

CONTROL OF ANODIC PASSIVATION SYSTEMS

BACKGROUND OF THE INVENTION

This invention relates to the control of an anodic passivation system. More particularly, this invention relates to a method of controlling the anodic passivation of a heat exchanger which contains corrosive fluids.

DESCRIPTION OF THE PRIOR ART

Through the years numerous attempts have been made to reduce the corrosion within vessels that contain corrosive fluids such as acids. The search has principally centered upon the effort to provide new metal alloys whose composition would resist the corrosion of specific fluids.

While such efforts have paired metal alloys and corrosive fluids such that corrosion rates were reduced, such efforts are not completely satisfactory. Anodic protection has been developed to offer further protection in some chemical environments against corrosion to vessels such as heat exchangers. For anodic protection one or more cathodes are placed within the heat exchanger and an electrical potential is established between the cathode and the anode which consists of the interior heat exchanger surfaces which are exposed to the corrosive fluid. The electrical potential between the cathode and the heat exchanger surfaces will passivate the surfaces which reduces or prevents corrosion of the protected metal surfaces. It has been found that anodic protection is particularly useful for the protection of heat exchangers which are used in sulfuric acid plants.

The potential must be maintained within the passive region of the polarization curve to effectively protect metallic surfaces. As the potential is increased, a region of low corrosion or passivity is reached. If the potential is increased further, a region of transpassivity and increased corrosion is reached. Thus it is understood that the passive region includes only a narrow range of potentials.

Even though anodic protection is extremely useful, it currently does not provide a complete solution to the problem of corrosion. Increased temperatures are being used in sulfuric acid plants today as a result of increased concerns for the recovery of energy. In addition to higher temperatures, the process conditions including water flow rates and temperatures into heat exchangers are often varied rather than maintaining relatively constant conditions as was done in the past. It has been found that anodic protection systems are unstable when the fluid temperature, and the vessel temperature, are fluctuating. Thus existing control schemes are not capable of maintaining the entire heat exchanger at the desired conditions for optimum reduction of corrosion.

SUMMARY OF THE INVENTION

It is an object of this invention to provide an apparatus and method for controlling an anodic protection system.

It is a further object of this invention to provide an apparatus and method for controlling an anodic protection system for use in a heat exchanger.

It is yet another object of this invention to provide an apparatus and method for controlling an anodic protection system in a heat exchanger in sulfuric acid service that is used to heat water to higher temperatures.

These and other objects are obtained by the control system of this invention and its method of operation.

The apparatus for controlling an anodic protection system to reduce the corrosion in a heat exchanger for sulfuric acid service includes a heat exchanger and an anodic protection system. The heat exchanger is typically a shell and tube heat exchanger in which the sulfuric acid passes through the shell side and the cooling or heating fluid passes through the tubes. The cathode of the anodic protection system is one or more electrodes which are aligned along the longitudinal axis of the heat exchanger and are symmetrically grouped about the axis. The cathode extends substantially the entire length of the heat exchanger. The interior surfaces of the heat exchanger are the anode of the anodic passivation system. A first reference electrode to measure the passivation of the heat exchanger is located near the first end of the heat exchanger and a second reference electrode is located near the second or opposite end of the heat exchanger from the first reference electrode. The output of the first reference electrode is measured by a first controller which is used to vary the output of a power supply connected to the cathode and to the shell of the heat exchanger. The power supply provides a voltage, and a corresponding current, between the cathode and the shell of the heat exchanger to provide passivation of the interior surfaces of the of the heat exchanger including the shell and the tubes. The output of the second reference electrode is measured by a second controller which provides an output used to change the set point or control point of the first controller so that the electrical power supply to the cathode will vary to provide a more consistent pattern of anodic passivation throughout the interior of the heat exchanger.

The invention also comprises a method of controlling an anodic protection system in a heat exchanger comprising:

(a) installing at least one cathode within the heat exchanger, the at least one cathode being aligned with the longitudinal axis of the heat exchanger and extending substantially along the length of the heat exchanger;

(b) installing a first reference electrode within the heat exchanger, the first reference electrode having a first controller having a set point for control and a power supply having an output creating an electrical potential between the at least one cathode and the heat exchanger;

(c) measuring the electrical potential of the heat exchanger with the first reference electrode;

(d) operating the first controller in response to measurements made by the first reference electrode to change the output of the power supply;

(e) installing a second reference electrode within the heat exchanger separated from the first reference electrode, the second reference electrode having a second controller;

(f) measuring the electrical potential of the heat exchanger with the second reference electrode;

(g) operating the second controller to vary its output signal in response to measurements made by the second reference electrode; and (h) using the output signal from the second controller to vary the set point of the first controller to shift the operation of the anodic protection system to maintain the heat exchanger substantially within the passive region of the polarization curve.

DESCRIPTION OF THE PREFERRED EMBODIMENT

Figure 1:
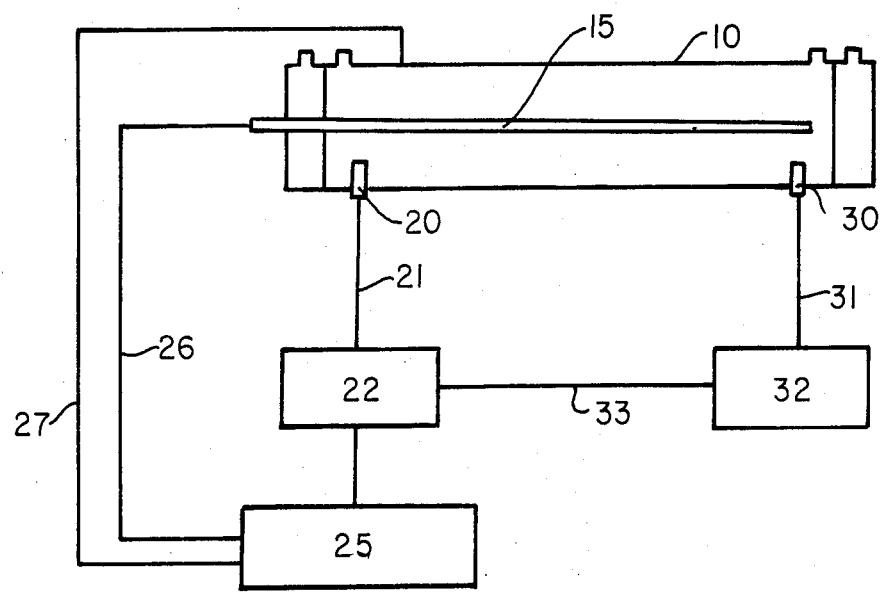
FIG. 1 shows a block diagram of the heat exchanger and the control scheme of this invention.

Turning now to FIG. 1, a heat exchanger 10 is shown. The heat exchanger 10 is typically fabricated of stainless steel for sulfuric acid service. The heat exchanger 10 is shown as a shell and tube configuration, although the tubes are not shown in this representation; however, a plate type heat exchanger may also be used. A cathode 15 for the anodic protection system extends parallel to the longitudinal axis of the heat exchanger 10. The cathode 15 is shown as a single electrode located at the longitudinal axis of the heat exchanger 10; however, the cathode 15 may be two or a plurality of electrodes which are symmetrically spaced about the longitudinal axis of the heat exchanger 10. The cathode 15 extends from one end of heat exchanger 10 into the shell and extends substantially the entire length of the tube bundle within the heat exchanger. Alternatively, two shorter cathodes may be used. If so, the cathodes extend into the heat exchanger from both ends and are of sufficient length to reach relatively close to one another. The interior surfaces of heat exchanger 10, including the interior surface of the shell and the surfaces of the tubes, become the anode of the anodic protection system.

A first reference electrode 20 is shown extending through the shell of heat exchanger 10 to reach the interior. The first reference electrode 20 is usually located near the acid inlet to heat exchanger 10. The first reference electrode 20 measures the electrical potential at the interior surface of the shell of heat exchanger 10 in the proximity of the reference electrode to determine the passivity of the interior surface. Wire 21 transmits the measured electrical potential from first reference electrode 20 to first controller 22. The first controller 22 compares the electrical potential measured by first reference electrode 20 to a set point value, the control point, and, if there is a deviation, adjusts the output of power supply 25. The output of power supply 25 is connected by wires 26 and 27 to the cathode 15 and the anode, the surface of heat exchanger 10, respectively. Therefore, a change in the output of power supply 25 will change the potential between the cathode 15 and the anode, the surfaces of heat exchanger 10, to maintain the passivity of the interior surfaces by keeping the potential within the passive region of the polarization curve.

A second reference electrode 30 is shown extending through the shell of heat exchanger 10 into the interior at the opposite end of heat exchanger 10 from first reference electrode 20. The second reference electrode 30 is identical to first reference electrode 20 and provides the same type of measurement. The measured potential is transmitted through wire 31 to second controller 32 which compares the measured potential to a set point value.

First controller 22 and second controller 32 are connected to one another, shown here as wire 33, to provide a control system for the anodic protection of heat exchanger 10. The desired control point for controller 32, the set point of controller 32, is chosen to maintain the potential measured by second reference electrode 30 within the passive region of the polarization curve for the heat exchanger's material of construction, as required for effective operation of the anodic protection system. The output of second controller 32 is used to vary the control point of first controller 22. Thus second controller 32 shifts the set point of first controller 22 to operate the anodic passivation system so that the interior surface of heat exchanger 10, including the surface of the tubes, is kept within the passivation region of the polarization curve. The set point of first controller 22 will never shift to be outside the limits of the passive region.

The following discussion of the operation of the anodic passivation system of this invention shows the operation in a heat exchanger in a sufuric acid plant. If the anodic passivation system were used in another process, the operation of the anodic passivation system would remain the same.

Figure 2:
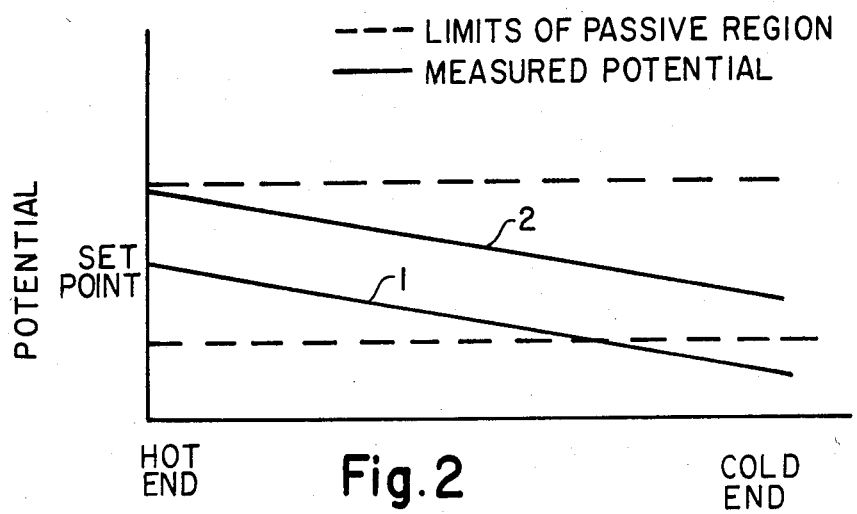
FIG. 2 shows a typical graphic plot for the initial anodic passivation potential in a heat exchanger having a uniform tube wall temperature along the length of the heat exchanger tubes.

FIG. 2 shows a graphic display of the method of controlling the anodic passivation of a heat exchanger in accordance with this invention. The graph has as its vertical axis the potential measured by the reference electrodes of the anodic protection system while the horizontal axis of the graph represents the length of the heat exchanger extending from its hot to its cold end. The horizontal dashed lines shown on the graph represent the upper and lower boundaries of the passive region of the polarization curve. Passivation of the metal of the heat exchanger occurs when the potential is accurately controlled to keep the surface of the metal within the passive region of the polarization curve. FIG. 2 represents the initial operation of a heat exchanger operated such that there is only a small temperature gradient between the temperature of the tube walls at each end of the heat exchanger. Curve 1 represents the operation of the anodic passivation system if second reference electrode 30 and second controller 32 are not used. First controller 22 operates to establish a potential between cathode 15 and the interior surfaces of heat exchanger 10 to passivate the metal to reduce the corrosion rate. First reference electrode 20 is located close to the hot end of heat exchanger 10, the end at which the hot acid enters the heat exchanger. A hot metal surface requires a greater current to passivate the surface than a cold metal surface. In this operation of heat exchanger 10, the temperature of the metal surfaces at the hot end of the heat exchanger may be similar to or only a few degrees warmer than the temperature of the metal surfaces at the cold end, thus the cold end of the heat exchanger requires the same, or nearly the same, current density as the hot end. To maintain the current density at the cold end of the heat exchanger nearly the same as the current density of the hot end of the heat exchanger, the potential at the cold end of the heat exchanger is lower than the potential at the hot end of the heat exchanger. Operation of heat exchanger 10 in this fashion, as shown by Curve 1, often had the potential at the hot end of the heat exchanger reaching the set point desired by first controller 22. At the cold end of the heat exchanger, however, the potential was often outside the limits of the passive region and the metal surfaces were therefore not protected by the anodic passivation system. The use of second reference electrode 30 and second controller 32 as required by this invention corrects the above problem in the operation of heat exchanger 10. Second reference electrode 30 which is located at the end of the exchanger 10 opposite first reference electrode 20 would measure a potential at the cold end of the heat exchanger as it approaches the limits of the passive region. Second controller 32 thus raises the set point of first controller 22 to require a greater output from power supply 25. The results of the changes made by second controller 32 are shown by Curve 2 which shows the results of the shift of the set point of first controller 22. The set point of first controller 22 will never shift to be outside the limits of the passive region, however. Raising the set point of first controller 22 raises the measured potential along the entire length of heat exchanger 10 such that operation of the anodic protection system will keep the heat exchanger substantially within the limits of the passive region of the polarization curve.

Figure 3:
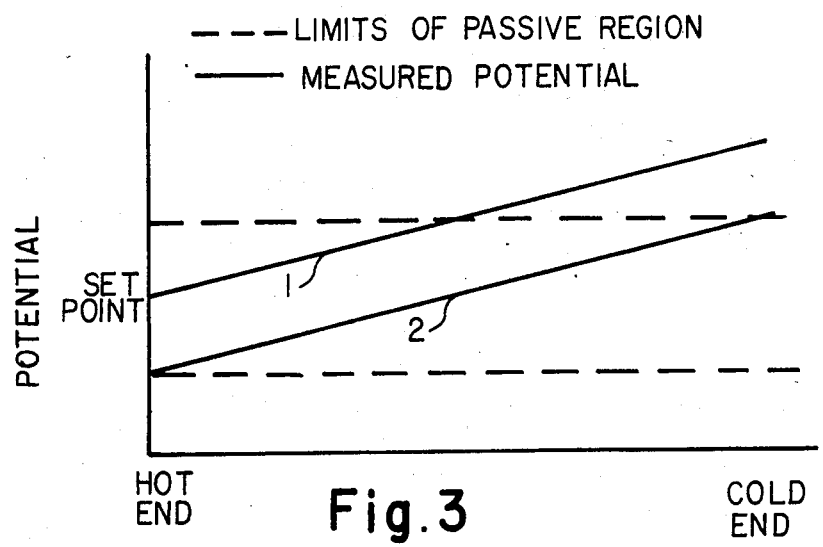
FIG. 3 shows a typical graphic plot for the initial anodic passivation potential in a heat exchanger having a large tube wall temperature gradient along the length of the heat exchanger tubes.

FIG. 3 also shows a graphic portrayal of the method of operating the anodic passivation system of this invention. FIG. 3 is an example of operation of a heat exchanger in which there is a large temperature gradient between the temperature of the tube walls at the hot end of the heat exchanger and the temperature of the tube walls at the cold end of the heat exchanger. The set point for first controller 22 operates power supply 25 to provide a potential between cathode 15 and the surfaces of heat exchanger 10. The hotter end of the heat exchanger requires a greater current density to passivate the metal surfaces than does the cold end of the heat exchanger. With a large temperature gradient the cold end of the heat exchanger requires a much lower current density than does the hot end of the heat exchanger. Curve 1 in FIG. 3 represents the operation of the anodic protection system without the help of second reference electrode 30 and second controller 32. The hot end of the heat exchanger 10 requires such a high current flow to passivate the metal surfaces that the cold end is overpowered and the potential is driven above the maximum limit of the passive region of the polarization curve so that the metal surfaces are not passivated and corrosion may take place. The use of second reference electrode 30 recognizes this problem and second controller 32 lowers the set point of first controller 22. This lowers the power output from power supply 25 to shift the potential along the surface of the heat exchanger 10 downwardly. Thus by using second reference electrode 30 and second controller 32, the operation of the anodic protection system can be shifted to operate as shown by Curve 2, that is, to keep the heat exchanger substantially within the limits of the passive region so that all of the surfaces within heat exchanger 10 may be protected. The set point of first controller 22 will never shift to be outside the limits of the passivation region, however. It is also possible to see operations similar to those shown in FIG. 2 when there is a large tube wall temperature gradient between the hot end and the cold end of the heat exchanger if the cold end of the heat exchanger has not been sufficiently passivated as a result of variations in process conditions.

Most heat exchanger applications which use cooling water for the coolant operate with relatively low tube wall temperatures, for example approximately 70° C., and relatively constant water flow rates and temperatures. Some heat exchanger applications in which the energy is recovered operate similarly with relatively high tube wall temperatures but with relatively uniform water flow rates and temperatures. In both these cases a single controller is sufficient to maintain the heat exchanger entirely within the passive region of the polarization curve.

However, many heat exchanger applications for the recovery of energy, such as by heating water to a temperature between 70° and 110° C., are operated to meet the requirements of the utility or water side of the heat exchanger. In these cases the maximum tube wall temperatures are relatively high, for example 100° C., and the water flow rates and temperatures can fluctuate widely and rapidly. At high tube wall temperatures the initial high current flow between the cathode and the surfaces of the heat exchanger result in a high voltage drop along the length of the heat exchanger and the entire passive region must be utilized to maintain substantially all of the heat exchanger surface within the passive region, that is, one end of the heat exchanger may be near the maximum limit of the passive region while the other end of the heat exchanger is near the minimum limit of the passive region. Under these conditions a single controller is not sufficient to keep substantially all of the heat exchanger surface within the passive region. The use of two controllers as taught by this invention is necessary.

The problems of control may be shown more easily by considering a specific example. The following data is typical for a heat exchanger fabricated from Type 304 stainless steel which contains sulfuric acid with a concentration of 98%. Similar behavior will be seen when Type 316 stainless steel is used. In normal practice the tube wall temperature within the heat exchanger is typically less than 70° C. The temperatures are relatively constant as fluid flow rates and fluid temperatures are constant. The anodic passivation system is able to control within the passive region which is approximately 0 to approximately 0.5 volts relative to a platinum reference electrode. At start-up of the heat exchanger, or when the heat exchanger is not passivated, the current density in this passive region is within the range of approximately 3 to approximately 10 microamps per square centimeter (3–10 $\mu A/cm^2$).

In the new high temperature applications such as the present invention is is meant to control, the tube wall temperatures within the heat exchanger are typically 100° C. or higher. At this temperature it has been determined that the passive region for the anodic protection system is still about 0 to 0.5 volts relative to a platinum reference electrode. However, at start-up or when the heat exchanger is not passivated the current density in the portions of the heat exchanger operating at this elevated temperature are within the range of approximately 30 to approximately 100 microamps per square centimeter (30 to 100 $\mu A/cm^2$).

After passivation of the heat exchanger the current density is less than 1.0 microamp per square centimeter in both of the above situations. Complete passivation requires that the heat exchanger be held within the limits of the passive region for a period of from several days to several weeks depending upon process conditions.

The foregoing description of the embodiments of this invention is not intended as limiting of the invention. As will be apparent to those skilled in the art, many variations on and modifications to the embodiments described above may be made without departure from the spirit and scope of this invention.

I claim:

1. A method of controlling an anodic protection system in a heat exchanger comprising:
    (a) installing at least one cathode within said heat exchanger, said at least one cathode being aligned with the longitudinal axis of said heat exchanger and extending substantially along the length of said heat exchanger;
    (b) installing a first reference elechrode within and at one end of said heat exchanger, said first reference electrode having a first controller having a set point for control and a power supply having an output creating an electrical potential between said at least one cathode and said heat exchanger;
    (c) measuring the electrical potential of said heat exchanger with said first reference electrode;
    (d) operating said frist controller in response to measurements made by said first reference electrode to change the output of said power supply;
    (e) installing a second reference electrode within and at the opposite end of said heat exchanger separated from said first reference electrode, said second reference electrode having a second controller;
    (f) measuring the electrical potential of said heat exchanger with said second reference electrode;
    (g) operating said second controller to vary its output signal in response to measurements made by said second reference electrode; and
    (h) using the output signal from said second controller to vary the set point of said first controller to shift the operation of the anodic protection system to maintain said heat exchanger substantially within the passive region of the polarization curve.

2. The apparatus for controlling an anodic protection system in a heat exchanger comprising:
    (a) at least one cathode within said heat exchanger, said at least one cathode being aligned along the longitudinal axis and extending substntially the length of said heat exchanger;
    (b) a power supply having an output connected to create an electrical potential between said at least one cathode and said heat exchanger;
    (c) a first reference electrode located within and at one end of said heat exchanger to measure the electrical potential of said heat exchanger;
    (d) a second reference electrode located within and at the opposite end of said heat exchanger to measure the electrical potential of said heat exchanger;
    (e) a first controller connected between said first reference electrode and said power supply, said first controller varying the output of said power supplying response to the measurements made by said first reference electrode; and
    (f) a second controller connected between said second reference electrode and said first controller, said second controller changing the control point of said first controller in response to the measurements made by said second reference electrode to shift the operation of the anodic protection system to maintain the heat exchanger substantially within the passive region of the polarization curve.

3. The apparatus of claim 2 wherein said at least one cathode comprises a plurality of electrodes symmetrically grouped about the longitudinal axis of said heat exchanger.

* * * * *